United States Patent [19]

Burford et al.

[11] Patent Number: 4,824,859
[45] Date of Patent: Apr. 25, 1989

[54] PYRAZOLINE COMPOUNDS COMPOSITIONS AND USE

[75] Inventors: Sidney C. Burford; David N. Hardern, both of Loughborough, United Kingdom

[73] Assignee: Fisons plc., Ipswich, England

[21] Appl. No.: 606,867

[22] Filed: May 3, 1984

[30] Foreign Application Priority Data

May 21, 1983 [GB] United Kingdom ............... 8314111
Dec. 22, 1983 [GB] United Kingdom ............... 8334283

[51] Int. Cl.$^4$ ................... A61K 31/415; C07D 231/06
[52] U.S. Cl. ................... 514/403; 514/333; 514/341; 546/256; 546/279; 548/362; 548/379
[58] Field of Search ............ 548/362, 379; 546/256, 546/279; 424/263, 273 P; 514/333, 341, 404, 407, 403

[56] References Cited

U.S. PATENT DOCUMENTS 4,564,684 1/1986 Copp et al. ..................... 548/379

Primary Examiner—Robert W. Ramsuer
Attorney, Agent, or Firm—Marshall, O'Toole, Gerstein, Murray & Bicknell

[57] ABSTRACT

There are described compounds of formula I,

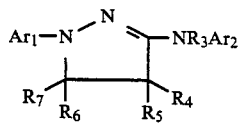

in which $Ar_1$ and $Ar_2$, which may be the same or different, each independently represent phenyl or pyridinyl, the phenyl or the pyridinyl each optionally being substituted by one or more of halogen; hydroxy; —$COOR_{12}$; trihalomethyl; alkoxy C1 to 6; alkyl C1 to 6; —$NR_1R_2$; alkoxy C1 to 6 substituted by —$NR_1R_2$ or by phenyl; or alkyl C1 to 6 substituted by —$NR_1R_2$ or by —$COOR_{12}$;

$R_1$ and $R_2$, which may be the same or different, each independently represent hydrogen or alkyl C1 to 6, $R_3$ represents hydrogen, alkyl C1 to 6, alkanoyl C1 to 6, benzoyl, —$COOR_8$, or —$CONHR_{11}$, $R_4$, $R_5$, $R_6$ and $R_7$, which may be the same or different each independently represent hydrogen, alkyl C1 to 6 or phenyl, $R_8$ represents alkyl C1 to 6 or aryl, $R_{11}$ represents alkyl C1 to 6 or aryl, $R_{12}$ represents hydrogen or alkyl C1 to 6, and pharmaceutically acceptable derivatives thereof.

There are also described compositions containing the compounds and methods for their preparation.

The compounds are indicated for use as pharmaceutical, eg antiinflammatory agents.

7 Claims, No Drawings

PYRAZOLINE COMPOUNDS COMPOSITIONS AND USE

This invention relates to new compounds, processes for their preparation and compositions containing them.

According to our invention we provide the compounds of formula I,

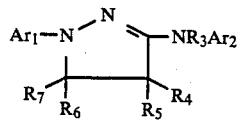
I in which $Ar_1$ and $Ar_2$, which may be the same or different, each independently represent phenyl or pyridinyl, the phenyl or the pyridinyl each optionally being substituted by one or more of halogen; hydroxy; $-COOR_{12}$; trihalomethyl; alkoxy C1 to 6; alkyl C1 to 6; $-NR_1R_2$; alkoxy C1 to 6 substituted by $-NR_1R_2$ or by phenyl; or alkyl C1 to 6 substituted by $-NR_1R_2$ or by $-COOR_{12}$;

$R_1$ and $R_2$, which may be the same or different, each independently represent hydrogen or alkyl C1 to 6, $R_3$ represents hydrogen, alkyl $C_1$ or 6, alkanoyl C1 to 6, benzoyl, $-COOR_8$, or $-CONHR_{11}$, $R_4$, $R_5$, $R_6$ and $R_7$, which may be the same or different each independently represent hydrogen, alkyl C1 to 6 or phenyl, $R_8$ represents alkyl $C_1$ to 6 or aryl, $R_{11}$ represents alkyl C1 to 6 or aryl, $R_{12}$ represents hydrogen or alkyl C1 to 6, and pharmaceutically acceptable derivatives thereof.

According to our invention we also provide a process for the preparation of the compounds of formula I, or a pharmaceutically acceptable derivative thereof which comprises (a) producing a compound of formula I in which $R_3$ represents hydrogen or alkyl C1 to 6, by reacting a compound of formula II,

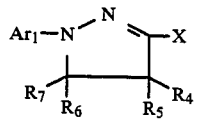
II in which $Ar_1$, $R_4$, $R_5$, $R_6$ and $R_7$ are as defined above, and X is a good leaving group,
with a compound of formula III,

III in which $R_{3a}$ represents hydrogen or alkyl C1 to 6, and $Ar_2$ is as defined above, (b) producing a compound of formula I, in which $R_3$ represents alkanoyl C1 to 6, benzoyl, or $-COOR_8$ by reacting a compound of formula I, in which $R_3$ represents hydrogen, with a compound of formula IV,

IV in which $R_{3b}$ represents alkanoyl C1 to 6, benzoyl or $-COOR_8$ and Y represents a good leaving group, (c) producing a compound of formula I, in which $Ar_1$ or $Ar_2$ bears a hydroxyl group, by selectively hydrogenating a corresponding compound of formula I, bearing a benzyloxy group, (d) producing a compound of formula I, in which $Ar_1$ or $Ar_2$ bears an alkoxy C1 to 6, or an alkoxy C1 to 6 substituted by $-NR_1R_2$ or phenyl, by reacting a corresponding compound of formula I bearing a hydroxy group, in the presence of a proton acceptor, with a compound of formula V,

V in which $R_{15}$ reprsents alkyl C1 to 6 or alkyl C1 to 6 appropriately substituted by $-NR_1R_2$ or phenyl and $Y_1$ represents a good leaving group, or (e) producing a compound of formula I, in which $R_3$ represents $CONHR_{11}$, by reacting a corresponding compound of formula I in which $R_3$ represents hydrogen, with a compound of formula VI, $$R_{11}N=C=O \qquad VI$$

in which $R_{11}$ is as defined above, and where desired or necessary converting the compound of formula I to a pharmaceutically acceptable derivative thereof or vice versa.

In process (a) good leaving groups that X may represent include halogen, e.g. chlorine or bromine, arylsulphonyl, hydroxy and esters thereof, alkoxy, e.g. methoxy or ethoxy, dihalophosphoryl, e.g. dichloro- or dibromo-phosphoryl, and $-NR_9R_{10}$, where $R_9$ and $R_{10}$ may each independently represent hydrogen or alkyl C1-6.

The compounds of formula II may, in certain cases, exist in tautomeric forms. For example, when X represents hydroxy, the compound of formula II may exist as a mixture of tautomers of formula A and formula B,

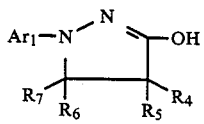
A

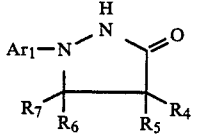
B

The reaction may be carried out with or without a solvent. When the reaction is carried out using a solvent, the solvent is preferably inert to the conditions of the reaction, for example a polar aprotic solvent such as 1,4-dioxan, acetonitrile or dimethylformamide. The reaction may be carried out at a temperature of from about 25° to 150° C.

The reaction of process (b) may be carried out in a solvent which is inert to the conditions of the reaction, for example a halogenated hydrocarbon, e.g. dichloromethane or dichloroethane; dimethylformamide or 1,4-dioxan. The reaction may be carried out at a temperature of from 0° to 125° C. The reaction may be carried out in the presence of an additional compound capable of accepting protons, eg a base, such as triethylamine or potassium carbonate.

Good leaving groups that Y may represent include halide, particularly chloride, and alkanoylate.

The selective hydrogenation of process (c) may be carried out using hydrogen in the presence of a suitable catalyst, eg palladium on charcoal. When hydrogen gas is used, the reaction is preferably carried out at a pressure of 1 to 5 atmospheres at a temperature of from about 0° to 100° C. in a solvent which is inert to the conditions of the reaction, eg ethanol or acetic acid.

In process (d), suitable proton acceptors include bases, for example metal alkoxides, eg potassium t-butoxide, metal carbonates, eg potassium carbonate, and trialkylamines, eg triethylamine. The reaction is preferably carried out in a solvent which is inert to the reaction conditions. Polar solvents are particularly preferred, eg dimethylformamide, 1,4 dioxan, tetrahydrofuran and N-methylpyrrolidinone. The reaction may be carried out at a temperature of from about 0° to 150° C. Leaving groups that $Y_1$ may represent include those described above for Y; chloride is particularly preferred.

The reaction of process (e) may be carried out in a solvent which is inert to the reaction conditions, eg a polar aprotic solvent. Suitable solvents include tetrahydrofuran, 1,4-dioxan and dimethylformamide. The reaction is preferably carried out at a temperature of from about 0° to 100° C.

Compounds of formula II, in which $R_4$ and $R_5$ each represent alkyl C1 to 6 or phenyl, X represents —OH, and $Ar_1$, $Ar_2$, $R_3$, $R_6$ and $R_7$ are as defined above, may be prepared by reacting a compound of formula VII,

   VII in which $Ar_1$ is as defined above, with a compound of formula VIII,

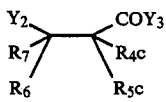   VIII in which $R_{4c}$ and $R_{5c}$ each independently represent alkyl C1 to 6 or phenyl, $Y_2$ and $Y_3$ each independently represent good leaving groups, and $R_6$ and $R_7$ are as defined above.

Good leaving groups that $Y_2$ and $Y_3$ may represent include those given for Y and $Y_1$ above; chloride is a particularly preferred leaving group. The reaction may be carried out in a solvent inert to the reaction conditions, eg in a halogenated hydrocarbon such as dichloromethane, at a temperature of from 0° to the reflux temperature of the solvent. The reaction is preferably carried out in the presence of a proton acceptor, eg a base such as triethylamine.

The compounds of formulae III, IV, V, VI, VII, VIII and the remaining compounds of formula II are either known, or may be made from known compounds using conventional techniques known per se.

The acid addition salts of the compounds of formula I may be prepared by reaction of the free-base with an appropriate acid. The acid addition salts may be converted to the corresponding free-base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable acid addition salts. Suitable salts include salts of mineral acids, for example, hydrohalic acids, e.g. hydrochloric acid or hydrobromic acid, or organic acids, e.g. formic, acetic or lactic acids. The acid may be polybasic, for example sulphuric, fumaric or citric acid. When the compound of formula I includes a group —$COOR_{12}$ or —$COOR_8$, pharmaceutically acceptable derivatives include pharmaceutically acceptable salts, esters and amides. Suitable salts include ammonium, alkali metal (eg sodium, potassium and lithium) and alkaline earth metal (eg calcium or magnesium) salts, and salts with suitable organic bases, eg salts with hydroxylamine, lower alkylamines such as methylamine or ethylamine, with substituted lower alkylamines, eg hydroxy substituted alkylamines such as tris(hydroxymethyl) methylamine, with simple monocyclic nitrogen heterocyclic compounds, eg piperidine or morpholine, with an amino acid, eg lysine, ornithine, arginine, or an N-alkyl, especially an N-methyl derivative of any one thereof, or with an aminosugar, eg glucamine, N-methylglucamine or glucosamine. Suitable esters include simple lower alkyl esters, eg the ethyl ester, esters derived from alcohols containing basic groups, eg di-lower alkyl amino substituted alkanols such as the 2-(diethylamino)-ethyl ester, and acyloxy alkyl esters, eg a lower acyloxy-lower alkyl ester such as the pivaloyloxymethyl ester. The pharmaceutically acceptable acid addition salts of the basic esters, eg the hydrochloride, the hydrobromide, the maleate or the fumarate salts, may also be used. The esters may be made by conventional techniques, eg esterification or transesterification. The amides may be, for example, unsubstituted or mono- or di- C1 to 6 alkyl or phenyl amides and may be made by conventional techniques, eg reactin of an ester of the correspnding acid with ammonia or an appropriate amine.

Other pharmaceutically acceptable derivatives are compounds which will be suitable bioprecursors (prodrugs) of the compounds of formula I and will be readily apparent to those skilled in the art and may be made from the compounds of formula I using conventional processes known per se or by processes analogous to those described above.

The compounds of formula I, and pharmaceutically acceptable derivatives thereof, are useful because they possess pharmacological activity in animals. In particular, the compounds are useful as anti-inflammatory agents as indicated in the following assay systems:

(a) rat carrageenan induced oedema, Winter et al, Proc. Soc. Exp. Biol. 111, 544 (1962), (b) inhibition of lipoxygenase, in the presence of exogenous arichidonic acid and measuring enzymic products by High Performance Liquid Chromatography, after the method of B A Jakschik et al, Biochemical and Biophysical Research Communications, 95 (1), 103, (1980), (c) inhibition of prostaglandin synthetase, utilising bovine seminal vesical microsomes as the enzyme source, and C-14 labelled arachidonic acid as substrate. The products are separated by thin layer chromatography and measured by scintillation counting, after the method of R W Egan, J L Humes, S A Kuehl, Biochemistry 17, 2230 (1978)

(d) topical treatment of ocular inflammation, European patent application 0022578A.

The compounds are indicated for use in the treatment or prophylaxis of inflammatory conditions in mammals, including man. Conditions that may be specifically mentioned are: rheumatoid arthritis, rheumatoid spondylitis, osteoarthritis, gouty arthritis, adjuvant arthritis and other arthritic conditions, inflamed joints;

eczema, psoriasis or other inflammatory skin conditions such as sunburn;

inflammatory eye conditions including conjunctivitis;

lung disorders in which inflammation is involved, eg bronchitis, pigeon fancier's disease and farmer's lung;

conditions of the gastrointestinal tract including aphthous ulcers, gingivitis, Crohn's disease (a condition of the small, and sometimes also of the large intestine), atrophic gastritis and gastritis varialoforme (conditions of the stomach), ulcerative colitis (a condition of the large intestine and sometimes the small intestine) coeliac disease (a condition of the small intestine), regional ileitis (a regional inflammatory condition of the terminal ileum), peptic ulceration (a condition of the stomach and duodenum) and irritable bowel syndrome;

pyresis, pain;

and other conditions associated with inflammation, particularly those in which lipoxygenase and cyclooxygenase products are a factor.

For the above mentioned uses the dosage administered will, of course, vary with the compound employed, the mode of administration and the treatment desired. However, in general satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 7.0 mg to 1,400 mg and unit dosage forms suitable for oral administration comprise from 2.0 mg to 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral, parenteral or topical administration. Thus the new compounds may be compounded with inorganic or organic, pharmaceutically acceptable adjuvants, diluents or carriers. Examples of such adjuvants, diluents and carriers are:- for tablets and dragées: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, ie oesophageal administration include tablets, capsules and dragees;

compositions in a form suitable for administration to the lung include aerosols, particularly pressurised aerosols;

compositions in a form suitable for administration to the skin include creams, eg oil-in-water emulsions or water-in-oil emulsion;

compositions in a form suitable for administration to the eye include drops and ointments.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, more selective, are more potent, produce less side effects or have other useful pharmacological properties, than compounds of similar structure.

Groups that $Ar_1$ and $Ar_2$ may represent include phenyl, 2-, 3- and 4-pyridyl.

When $Ar_1$ or $Ar_2$ represent a substituted phenyl, or a substituted 2-, 3- or 4-pyridinyl, $Ar_1$ or $Ar_2$ preferably bears one, two or three substituents, which may be the same or different, selected from halogen, eg fluorine, chlorine or bromine; hydroxy, trihalomethyl, eg trichloromethyl, and especially trifluoromethyl; alkoxy C1 to 6, particularly alkoxy C1 to 4, especially methoxy, ethoxy or propyloxy; alkyl C1 to 6, particularly alkyl C1 to 4, especially methyl, ethyl or propyl; or $-NR_1R_2$. Alkyl groups that $R_1$ or $R_2$ may each independently represent include methyl, ethyl, propyl and butyl. Particular groups that $-NR_1R_2$ may represent are $-N(CH_3)_2$ and $-N(CH_2CH_3)_2$.

Other substituents that $Ar_1$ or $Ar_2$ may bear include alkyl C1 to 6 in which the alkyl is substituted by $-NR_1R_2$, eg methyl, ethyl or propyl substituted by $-N(CH_3)_2$ or $-N(CH_2CH_3)_2$. A particularly preferred substituent is $-CH_2N(CH_2CH_3)_2$.

$Ar_1$ or $Ar_2$ may be substituted by alkyl C1 to 6 in which the alkyl is substituted by $-COOR_{12}$, wherein $R_{12}$ represents alkyl C1 to 6, preferably alkyl C1 to 4, eg methyl, ethyl or propyl. Typical substituents that may be mentioned include $-CH_2CO_2CH_3$, $-CH_2CH_2CO_2C_2H_5$, $-CH_2CH_2CH_2CO_2C_2H_5$.

$Ar_1$ or $Ar_2$ may be substituted by alkoxy C1 to 6, in which the alkoxy is substituted by $NR_1R_2$. The alkyl group is preferably alkyl C1 to 4, eg methyl, ethyl or propyl. $R_1$ and $R_2$ preferably represent alkyl C1 to 4, eg methyl, ethyl or propyl. Substituents that may be particularly mentioned include $-(CH_2)_2N(CH_2CH_3)_2$.

Specific groups that $Ar_1$ and $Ar_2$ may represent include:
phenyl,
4-chlorophenyl,
4-methoxyphenyl,
4-dimethylaminophenyl,
3-trifluoromethylphenyl,
4-methylphenyl,
3-hydroxy-4-propylphenyl,
3,4-dichlorophenyl,
4-carboxyphenyl,
4-(diethylaminoethoxy)phenyl,
4-benzyloxyphenyl,
2-and 3-pyridinyl,
4-methyl-2-pyridinyl,
4-hydroxyphenyl,
4-diethylaminomethylphenyl and
4-(carboxymethyl)methylphenyl.

Preferred groups that $Ar_1$ may represent include phenyl or pyridinyl, the phenyl optionally being substituted by one or more of halogen, trihalomethyl or alkyl C1 to 6. A particularly preferred group is phenyl.

Preferred groups that $Ar_2$ may represent include phenyl or phenyl substituted by alkoxy C1 to 6 or by alkoxy C1 to 6 substituted by $-NR_1R_2$ or phenyl. Where the phenyl is substituted, the substituent is preferably in the 4-position.

When $R_3$ represents alkyl C1 to 6, $R_3$ may represent pentyl or hexyl and especially methyl, ethyl, propyl or butyl.

When $R_3$ represent alkanoyl C1 to 6, $R_3$ may represent pentanoyl or hexanoyl and especially formyl, acetyl, propionyl or butanoyl.

We particularly prefer compounds in which $R_3$ represents hydrogen or alkyl C1 to 6.

Aryl groups that $R_8$ and $R_{11}$ may represent include monocyclic benzenoid aromatics, e.g. phenyl.

Compounds of formula I in which one or more of $R_4$, $R_5$, $R_6$ and $R_7$ represent alkyl C1 to 6 that may be specifically mentioned include those in which one or more of $R_4$, $R_5$, $R_6$ and $R_7$ contain up to and including four carbon atoms, for example when one or more of $R_4$, $R_5$, $R_6$ and $R_7$ represent methyl, ethyl or propyl. Compounds that may be particularly mentioned are those in which $R_4$ and $R_5$ are identical and/or $R_6$ and $R_7$ are identical, eg when $R_4$ and $R_5$ both represent methyl, or when $R_6$ and $R_7$ both represent methyl.

Particular mention may also be made of compounds in which only one of the groups $R_4$, $R_5$, $R_6$ or $R_7$ is phenyl. We particularly prefer compounds in which only $R_6$ is phenyl.

We particularly prefer compounds in which either both $R_4$ and $R_5$ or both $R_6$ and $R_7$ represent alkyl C1 to 6.

Certain of the compounds of formula I possess one or more chiral centres and the invention also provides the compounds in the form of their individual optical isomers or as racemic or other mixtures thereof. Certain of the compounds of formula I may also exist as stereoisomers and in these cases the invention provides all stereoisomeric forms. The various isomers may be prepared and/or separated using conventional processes known per se.

The invention is illustrated but in no way limited by the following Examples, in which temperatures are in degrees Celsius.

EXAMPLE 1

4,5-dihydro-N-(4-methoxyphenyl)-1-phenyl-1H-pyrazol-3-amine

A mixture of 1-phenyl-[1H]-pyrazolidin-3-one (0.162 g), 4-methoxyaniline (0.37 g) and p-toluenesulphonic acid (0.17 g) was heated in an oil bath at 140° under a nitrogen atmosphere for 15 minutes. The reaction was cooled and the products dissolved in 1% sodium hydroxide solution and diethyl ether. The organic phase was separated and washed with 1% hydrochloric acid solution, water and then dried over sodium sulphate. The organic phase was filtered and evaporated to a pale oil which on trituration with pentane gave the title compound (0.1 g) m.p. 153°–4°.

Analysis: Found: C=71.91%, H=6.30%, N=15.74% $C_{16}H_{17}N_3O$ requires C=71.91%, H=6.41%, N=15.73%

EXAMPLE 2

1-(3-Trifluoromethylphenyl)-4,5-dihydro-N-(4-methoxy phenyl)-1H-pyrazol-3-amine

A mixture of 1-(3-trifluoromethylphenyl)-4,5-dihydro-1H-pyrazol-3-amine (0.23 g), 4-methoxyaniline (0.37 g) and p-toluenesulphonic acid (0.17 g) was heated in an oil bath at 140° under nitrogen for 15 minutes. The reaction was cooled, dilute hydrochloric acid and ether added and the organic phase separated, dried over sodium sulphate, filtered and evaporated to leave a yellow solid, which on trituration with pentane gave the colourless title compound (0.1 g) m.p. 127°–8°.

EXAMPLE 3

N-(4-Chlorophenyl)-4,5-dihydro-1-phenyl-1H-pyrazol-3-amine (a) 3-Chloro-4,5-dihydro-1-phenyl-1H-pyrazole 1-Phenylpyrazolidin-3-one (8.1 g) was suspened in dry toluene (100 ml), followed by addition of phosphoryl chloride (7.0 ml) and the mixture stirred for 1 hour at 85°. When cool the toluene was decanted from the solid and solvent removed in vacuo to give the sub-title compound, (6.9 g), mp 92°–93°.

(b) N-(4-Chlorophenyl)-4,5-dihydro-1-phenyl-1H-pyrazol-3-amine

3-Chloro-4,5-dihydro-1-phenylpyrazole (1.8 g) and 4-chloroaniline (3.8 g) were fused under $N_2$ at 140° for 20 minutes. The melt was cooled and the solid dissolved in $CH_2Cl_2$, washed with 1% HCl ($\times$3), water, dried ($Na_2SO_4$), then absorbed into silica and column chromatographed using first 1:1 petrol: ether and then ether to give the title product as a yellow powder (1.0 g), (37%), m.p. 144°–7°.

EXAMPLE 4

N-(4,5-dihydro-1-phenyl-1H-pyrazol-3-yl)-N-(4-methoxyphenyl)acetamide 1.7M n-butyl lithium in hexane (7.0 ml) was added dropwise to a solution of 4,5-dihydro-N-(4-methoxyphenyl)-1-phenyl-1H-pyrazol-3-amine (2.67 g) in tetrahydrofuran (150 ml) at −25° under $N_2$. After 40 minutes ethyl acetate was added and the solution was allowed to reach room temperature. After being stirred for 2 hours, the solution was evaporated to dryness and the residue chromatographed on silica gel eluting with ethyl acetate in dichloromethane to give an oil which crystallised on trituration with ether. The solid was recrystallised from ether and hexane to give the title compound (0.82 g) mp 83°–5° (dec).

Found: C=69.64%, H=6.12%, N=13.68%.

$C_{18}H_{19}N_3O_2$ requires: C=69.90%, H=6.15%, N=13.59%.

EXAMPLE 5

Ethyl N-(4,5-dihydro-1-phenyl-1H-pyrazol-3-yl)-N-(3-pyridinyl)carbamate

Ethylchloroformate (0.75 ml) was added dropwise to a solution of 4,5-dihydro-1-phenyl-N-(3-pyridinyl)-1H-pyrazol-3-amine (1.66 g) and triethylamine (2.85 ml) in tetrahydrofuran (150 ml) at −45° under $N_2$. The solution was allowed to warm to room temperature and stirred for 24 hours. The solution was filtered, evaporated to dryness, and the residue chromatographed on silica gel eluting with ethyl acetate in dichloromethane to give an oil which crystallised on triturating with ether. The solid was recrystallised from ether and petrol to give the title compound (0.66 g) mp 110°–12° (dec).

Found: C=65.54%, H=5.93%, N=17.96%.

$C_{17}H_{18}N_4O_2$ requires: C=65.80%, H=5.85%, N=18.06%.

EXAMPLE 6

N-[4-(2-diethylaminoethoxy)phenyl]-N-[4,5-dihydro-1-phenyl-1H-pyrazol-3-yl]-N'-phenylurea Phenylisocyanate (1.05 ml) was added dropwise to a solution of N-[4-(2-diethylaminoethoxy)phenyl]-4,5-dihydro-1-phenyl-1H-pyrazol-3-amine (2.4 g) in tetrahydrofuran (30 ml) and the solution heated to reflux for 4 hours. After cooling the solvent was removed and water added to the residue, which was then extracted with ether. The combined ether layer was washed with water and dried. Solvent was removed to give a solid which was recrystallised from ethyl acetate and petroleum ether to give the title compound (1.3 g) mp 140°–1°.

Found: C=71.35%, H=6.83%, N=14.84%.

$C_{28}H_{33}N_5O_2$ requires: C=71.33%, H=7.06%, N=14.86%.

EXAMPLE 7

4,5-Dihydro-N-(4-hydroxyphenyl-1-phenyl-1H-pyrazol-3-amine

A suspension of N-(4-benzyloxyphenyl)-4,5-dihydro-1-phenyl-1H-pyrazol-3-amine (6.9 g) in ethanol (350 ml) was hydrogenated at atmospheric pressure over 10% palladium on carbon until hydrogen uptake ceased. The mixture was filtered and the filtrate evaporated to small volume. The resulting precipitate was collected, washed with ethanol and dried to give the title compound, (3.32 g) mp 211°–14° (dec).

Found: C=71.16%, H=5.99%, N=16.59%.

$C_{15}H_{15}N_3O$ requires: C=71.11%, H=5.97%, N=16.60%.

EXAMPLE 8

N-[4-(2-diethylaminoethoxy)phenyl]-4,5-dihydro-1-phenyl-1H-pyrazol-3-amine 2E-butenedioate Potassium carbonate (6.92 g), 4,5-dihydro-N-(4-hydroxyphenyl)-1-phenyl-1H-pyrazol-3-amine (4.22 g) and 2-diethylaminoethylchloride hydrochloride (2.95 g) in dimethylformamide (30 ml) were stirred together at room temperature for 25 hours. The reaction mixture was then diluted with water and extracted with ethyl acetate. The combined extracts were washed with water and dried. Solvent was removed to give an oil which was redissolved in ether and a solution of fumaric acid (0.33 g) in ether added to give a precipitate. This was collected and dried to give the title compound, (4.2 g) mp 54°–56° (dec).

Found: C=63.49%, H=6.72%, N=12.14%.

$C_{25}H_{32}N_4O_5$ requires: C=64.10%, H=6.89%, N=11.86%.

EXAMPLE 9

4,4-Dimethyl-1-(2-pyridinyl)-3-pyrazolidinone

2-Pyridylhydrazine (10.9 g) in dichloromethane (120 ml) and dry triethylamine (28 ml) were chilled in an ice bath. -β-chloropivaloyl chloride (15.5 g) in dichloromethane (20 ml) was added dropwise with stirring for 15 minutes and the mixture was refluxed for 3 hours. When cool the triethylamine hydrochloride was filtered off and the filtrate evaporated to dryness and rinsed four times with the minimum quantity of ether to give the title compound (13.6 g) after recrystallisation from cyclohexane mp 141°–144°.

EXAMPLE 10

The following compounds were prepared from the corresponding 4,5-dihydro-1H-pyrazol-3-amine, using the method of Example 2:

(a) 1-(3,4-Dichlorophenyl)-4,5-dihydro-N-(4-methoxyphenyl)-1H-pyrazol-3-amine, mp 142°–4°, (b) 4,5-Dihydro-5,5-dimethyl-1-phenyl-N-(3-pyridinyl)-1H-pyrazol-3-amine, mp 147°–9°, (c) 4,5-Dihydro-5,5-dimethyl-N-(4-dimethylaminophenyl)-1-phenyl-1H-pyrazol-3-amine, mp 166°–7°, (d) 1-(3-Trifluoromethylphenyl)-4,5-dihydro-N-phenyl-1H-pyrazol-3-amine, mp 128°–9°, (e) (±)-4,5-Dihydro-1,5,N-triphenyl-1H-pyrazol-3-amine, mp 172°–3°, (f) (±)-4,5-Dihydro-1,5-diphenyl-N-(3-pyridinyl)-1H-pyrazol-3-amine, mp 168°–70°, (g) 1-(4-Chlorophenyl)-4,5-dihydro-N-(4-methylpyridin-2-yl)-1H-pyrazol-3-amine, mp 208°–10°, (h) 1-(4-Chlorophenyl-4,5-dihydro-N-(3-pyridinyl)-1H-pyrazol-3-amine, mp 234°–6°, (i) 1-(3-Trifluoromethylphenyl)-4,5-dihydro-N-(3-pyridinyl)-1H-pyrazol-3-amine, mp 235°–7° (dec), (j) N-(4-Benzyloxyphenyl)-4,5-dihydro-1-phenyl-1H-pyrazol-3-amine, mp 187°–8°, (k) 4-(4,5-Dihydro-1-phenyl-1H-pyrazol-3-yl)aminobenzoic acid, mp 232°–5°, (l) 4,5-Dihydro-1-phenyl-N-(3-pyridinyl)-1H-pyrazol-3-amine, mp 200°–202°, (m) 4,5-Dihydro-N-(4-dimethylaminophenyl)-1-phenyl-1H-pyrazol-3-amine, mp 142°–3°, (n) 4,5-Dihydro-N-(4-methoxyphenyl)-1-(4-methylphenyl)-1H-pyrazol-3-amine, mp 163°–165°, (o) 1-(4-Chlorophenyl)-4,5-dihydro-N-(4-methoxyphenyl)-1H-pyrazol-3-amine, mp 145°–146°, (p) N-[(4-Diethylaminomethyl)phenyl]-4,5-dihydro-1-phenyl-1H-pyrazol-3-amine 2E-butenedioate, mp 48°–52°, (q) (±)-4,5-Dihydro-N-(4-methoxyphenyl)-5-methyl-1-phenyl-1H-pyrazol-3-amine, mp 47°–50°, (r) 4,5-Dihydro-N-(4-methoxyphenyl)-4-methyl-1-phenyl-1H-pyrazol-3-amine, mp 97°–100°, (s) Methyl 4-[4,5-dihydro-1-phenyl-1H-pyrazol-3-yl]amino phenylacetate, mp 108°–109°, (t) 4,5-Dihydro-1,N-diphenyl-1H-3-amine, mp 155°–6°.

EXAMPLE 11

The following compounds were prepared from the corresponding 3-chloro-4,5-dihydro-1H-pyrazole, using the method of Example 3:

(a) 4,5-Dihydro-N-(4-methylphenyl)-1-phenyl-1H-pyrazol-3-amine, mp 145°–9°, (b) 4,5-Dihydro-N-methyl-1,N-diphenyl-1H-pyrazol-3-amine, mp 100°–102°, (c) 4,5-Dihydro-4,4-dimethyl-N-(4-dimethylaminophenyl)-1-phenyl-1H-pyrazol-3-amine, mp 155°–158°, (d) 4,5-Dihydro-N-(4-methoxyphenyl)-4,4-dimethyl-1-(2-pyridinyl)-1H-pyrazol-3-amine, mp 137°–9°, (e) 4,5-Dihydro-N-(4-methoxyphenyl)-4,4-dimethyl-1H-pyrazol-3-amine, mp 111°–112°, (f) 4,5-Dihydro-N-(4-methoxyphenyl)-5,5-dimethyl-1-phenyl -1H-pyrazol-3-amine, mp 112°–14°, (g) 4,5-Dihydro-N-(3-hydroxy-4-propylphenyl)-1-phenyl-1H-pyrazol-3-amine, mp 167°–70° (dec).

EXAMPLE 12

The following compound was prepared from the corresponding 1,N-diaryl-4,5-dihydro-1H-pyrazol-3-amine using the method of Example 5:

(a) Ethyl [N-(4-chlorophenyl)-4,5-dihydro-1H-pyrazol-3-yl]-N-[4-methoxyphenyl]carbamate, mp 92°–94°.

EXAMPLE 13

The following compound was prepared from the corresponding 1,N-diaryl-4,5-dihydro-1H-pyrazol-3-amine using the method of Example 6:

(a) N-[4,5-Dihydro-1-phenyl-1H-pyrazol-3-yl]-N-[3-pyridinyl]-N'-phenylurea, mp 163°–5°.

What we claim is:

1. A compound of formula I,

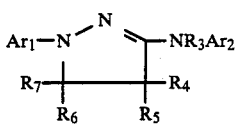

in which $Ar_1$ and $Ar_2$, which may be the same or different, each independently represent phenyl or pyridinyl, the phenyl or the pyridinyl each optionally being substituted by one or more of halogen; hydroxy; $COOR_{12}$; trihalomethyl; alkoxy C1 to 6; alkyl C1 to 6; —$NR_1R_2$; alkoxy C1 to 6 substituted by $NR_1R_2$ or by phenyl; or alkyl C1 to 6 substituted by $NR_1R_2$ or by —$COOR_{12}$;

$R_1$ and $R_2$, which may be the same or different, each independently represent hydrogen or alkyl C1 to 6, $R_3$ represents —$COOR_8$, or —$CONHR_{11}$, $R_4$, $R_5$, $R_6$ and $R_7$, which may be the same or different each independently represent hydrogen, alkyl C1 to 6 or phenyl, $R_8$ represents alkyl C1 to 6 or phenyl, $R_{11}$ represents alkyl C1 to 6 or phenyl, $R_{12}$ represents hydrogen or alkyl C1 to 6, or a pharmaceutically acceptable acid addition salt, ester, amide, or prodrug thereof.

2. A compound according to claim 1, wherein $Ar_1$ represents phenyl or pyridinyl, the phenyl being optionally substituted by one or more of halogen, trihalomethyl or alkyl C1 to 6.

3. A compound according to claim 1, wherein $Ar_2$ represents phenyl, the phenyl optionally being substituted by alkoxy C1 to 6 or by alkoxy C1 to 6 substituted by $NR_1R_2$ or phenyl.

4. A compound according to claim 1, wherein either both $R_4$ and $R_5$ or both $R_6$ and $R_7$ represent alkyl C1 to 6.

5. Ethyl N-(4,5-dihydro-1-phenyl-1H-pyrazol-3-yl), N-(3-pyridinyl)carbamate,

N-[4-(2-Diethylaminoethoxy)phenyl]-N-[4,5-dihydro-1-phenyl-1H-pyrazol-3-yl]-N'-phenylurea, Ethyl N-[(4-chlorophenyl)-4,5-dihydro-1H-pyrazol-3-yl]-N-[4-methoxyphenyl]carbamate, or N-[4,5-Dihydro-1-phenyl-1H-pyrazol-3-yl]-N-[3-pyridinyl]-N'-phenylurea.

6. A composition for treating an inflammatory condition comprising an effective amount of a compound according to any one of the preceding claims in admixture with a pharmaceutically acceptable adjuvant, diluent or carrier.

7. A method of treatment of an inflammatory condition, which comprises administration of an effective amount of a compound according to claim 1 to a patient suffering from such a condition.

* * * * *